United States Patent [19]

Shiokawa

[11] 4,059,902
[45] Nov. 29, 1977

[54] TRAY FOR PREPARING A DENTIFORM MODEL USED FOR AN OPERATION ON A DENTAL TECHNIC

[76] Inventor: Yoichi Shiokawa, No. 1, 206, Ooazaiwamurada, Saku, Nagano, Japan, 385

[21] Appl. No.: 683,457

[22] Filed: May 5, 1976

[30] Foreign Application Priority Data

May 7, 1975 Japan ................................. 51-8222

[51] Int. Cl.² .......................................... A61C 13/22
[52] U.S. Cl. ................................................. 32/11
[58] Field of Search ................. 32/11, 40 R; 425/180, 425/175, 179; 269/54, DIG. 1, 117, 118, 54

[56] References Cited

U.S. PATENT DOCUMENTS 3,495,333   2/1970   Kuhn ................................... 425/175

*Primary Examiner*—Robert Peshock
*Attorney, Agent, or Firm*—Frank J. Jordan

[57] ABSTRACT

A tray for preparing a dental model which includes an arcuate channel formed in a body and simulating the curvature of a row of teeth. A wedge shaped notch is provided in the channel for assisting removal of a hard body cast in the channel, and the notch is adapted to be filled with a soft substance prior to filling of the channel with a material which will set to form the hard body.

1 Claim, 4 Drawing Figures

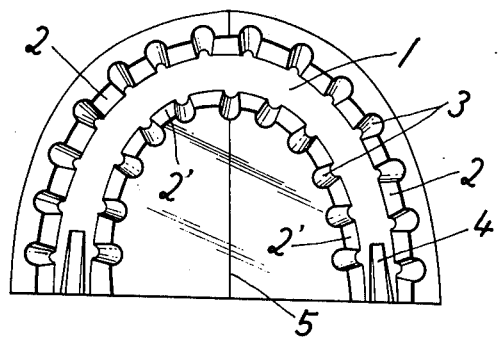
FIG.1
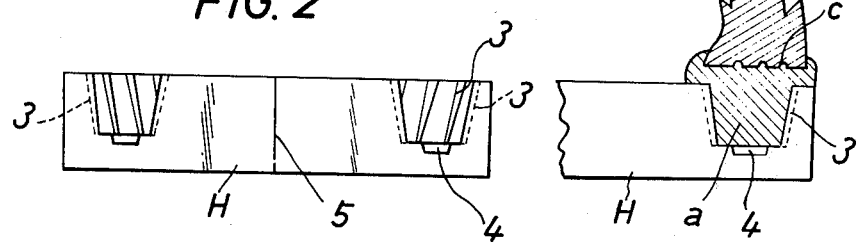
FIG.2
FIG.4
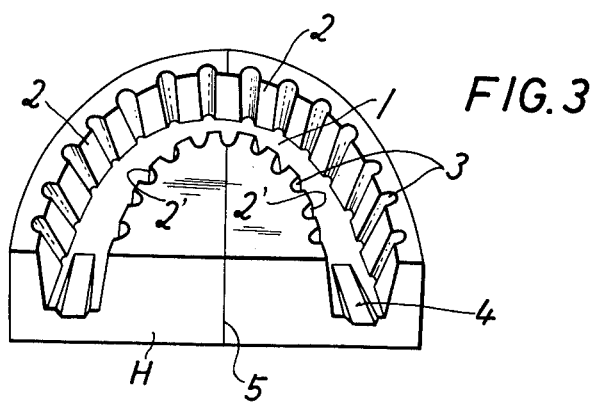
FIG.3

TRAY FOR PREPARING A DENTIFORM MODEL USED FOR AN OPERATION ON A DENTAL TECHNIC

BRIEF SUMMARY OF THE INVENTION

The present invention relates to a tray for preparing a dentiform model used for an operation on a dental technic.

Heretofore, known systems have respectively been conventionally used as a method of preparing a dentiform model for its use in parts. However, such systems have many defects such as being complicated in the fixing and arranging of the parts and also the difficulty in arranging the same in a parallel manner, as well as the difficulty in fixing and arranging the parts when the impressions of inlays or post crowns have been obtained; and, further, incidences of shearing of the parts upon revolution thereof are apt to be increased when the such parts are is often fixed or removed throughout an operation.

According to the one known system, the retention power of the core portion of a tray is weak and thus a position of a dentiform model would be out of order.

According to another known system all of the dentiform model must be removed from a tray when a divided individual tooth is removed from a row of the teeth; and, further, it is impossible to confirm by naked eye whether a supporting portion is elevated above the base of a tray when a divided dentiform model has been fixed and arranged in the original row of teeth; and, in addition, this system is complicated in its operation and expensive.

It is an object of the present invention provide a tray for preparing a divisional dentiform model easily and inexpensively, avoiding the defects of the existing systems. The tray according to the present invention comprises a tapered core portion of an inner surface of a supporting stand for maintaining and fixing a dentiform model, a tapered u-shaped groove having a longitudinal direction at regular distances along with an inner surface of the core portion, a wedged notch portion mounted on the base ends of a core portion and a center line of a tray.

These objects will be apparent from the drawing and the following discription thereof. Various modifications and changes in details of construction are comprehended within the scope of the appended claims.

A tray according to the present invention comprises a tapered core portion of an inner surface of a supporting stand for maintaining and fixing a dentiform model, a tapered u-shaped groove having a longitudinal direction at regular distances along with an inner surface of the core portion for readjusting a position of a supporting stand to the original line of teeth and preventing a divided dentiform model from falling off out of a supporting stand when the divided dentiform model is fixed and arranged, a wedged notch portion mounted on the base of both ends of a core portion for removing a supporting stand and a core portion having been filled up with hard plaster, and a center line on a tray for exactly positioning of another dentiform model on a supporting stand.

FIG. 1 is a plan view of a tray.
FIG. 2 is a front view of a tray.
FIG. 3 is a perspective view of a tray.
FIG. 4 is a partial explanatory vertical view in which hard plaster is filled up into a core portion 2 and a dentiform model of a line of the tooth are arranged and fixed thereon.

DETAILED DESCRIPTION OF THE INVENTION

According to the process of the present invention, a dentiform model having a supporting portion a may be prepared as set forth hereinunder in detail.

Utility wax is filled up into a wedged notch portion 4, and both opening ends of a core portion 1 are closed and covered by an adhesive tape. Isolating material is applied on the whole of an inner surface of a core portion 1 and a u-shape groove 3 and then the kneaded hard plaster is filled up thereinto. Thereafter, the base of a prearranged model of a row of teeth is planed by using a model trimmer and scored by a saw. After having been thoroughly moistened with water, the model is fixed on the hard plaster filled within a core portion 1 adjusting to a center line 5; and this is permitted to stand until the hard plaster has satisfactorily been hardened.

Thereafter, the adhesive tape on both opening ends is removed, and the supporting stand is easily removed by using a driver one after the other just as wrenching same open at an opening portion of said wedged notch portion 4. Thus, a model of a row of the teeth having a supporting stand may be obtained; and said model is used for an operation of a dental technic by cutting off the necessary tooth among a row of the teeth together with its supporting stand by using a saw.

In rearrangement of thus divided dentiform model into a core portion 1 for fixing thereof, said dentiform model may be arranged in the original row of the teeth by means of u-shaped groove; and accordingly there should be no fear of causing twisting or shearing in turning of a dentiform model. Further, said dentiform model arranged and fixed in a core portion 1 shall not easily be falling off therefrom because of having been supported by said u-shaped groove; and, if desired, it shall be even more thoroughly fixed by means of a sticky wax.

Thus, it is not necessary to take off the whole of a dentiform model out of a core portion 1 and it becomes possible to separately take off a divided dentiform model therefrom. In addition, by properly selecting the depth, width, and taper of a core portion 1 and the distance, width, and taper of u-shaped groove 3, a dentiform model shall not fall off from the core portion 1 without mounting a lock or a fixing nail thereon. Said model may be adjustable to any kind of an articulator by mounting a split cast on the back side of tray H; and any kind of a row of teeth may be incorporated in the model by preparing four sizes of tray H.

The material for said tray may be metals; however a transparent plastic is preferable because foaming of the plaster filled into the supporting stand or floating thereof due to mixing of wax or alien substances with the plaster may be and checked and confirmed from the outside of the tray H.

When the teeth are adjacent to each other on a supporting stand a, it is possible to divide the teeth in question by using a saw from the back of the supporting stand a.

Regarding the shape of the core portion 1, it is preferable and convenient to use different shape for each jaw, upper and lower, and a different shape for front teeth and molar teeth front teeth or molar teeth.

As the type of tray H is simple, plastic molding is easy, and a mass production becomes possible at low cost.

What I claim is:

1. A tray for preparing a dental model, the tray comprising a single, integral flat body, an arcuate channel formed in a flat surface of the body and simulating the curvature of a row of teeth, the channel having side walls which are outwardly tapered in the direction of said surface, substantially vertical grooves of arcuate cross section formed at regularly spaced intervals along the entire extent of each of the side walls, the arcuate channel also having a base and open ends and, formed in the base contiguous with each of the open ends of the channel, a respective wedge shaped notch for assisting removal by means of a driver blade of a hard body cast in the channel, the open ends of the channel being adapted to be closed by adhesive tape and the notches being adapted to be filled with a soft substance prior to the filling of the channel with a material which will set to form said hard body.

* * * * *